United States Patent [19]

Rizaev et al.

[11] 4,439,371

[45] Mar. 27, 1984

[54] METHOD FOR PREPARING PHTHALONITRILES

[76] Inventors: Ramiz G. K. O. Rizaev, ulitsa Sharif-Zade, 148, kv. 67; Mirabdulla M. O. Mirataev, ulitsa Patrisa Lumumby, 59 blok 1, kv. 20; Viktor E. Sheinin, ulitsa Pervomaiskaya, 251, kv. 28; Zemfira J. K. Magerramova, ultisa Chicherina, 6, kv. 11; Jury N. Litvishkov, ulitsa 28 Aprelya, 11, kv. 38; Sekher G. K. Gusein-Zade, ulitsa Basina, 53, kv. 42; Tofik S. O. Farzullaev, ulitsa B.Avakiana, 55, kv. 10; Nazaket M. K. Ilyasova, Moskovsky prospekt, 95a, kv. 39,, all of Baku, U.S.S.R.

[21] Appl. No.: 247,537

[22] Filed: Mar. 9, 1981

[51] Int. Cl.³ ............................................. C07C 120/14
[52] U.S. Cl. .................................................. 260/465 C
[58] Field of Search .................................... 260/465 C

[56] References Cited

U.S. PATENT DOCUMENTS 3,637,797  1/1972  Decker et al. ................... 260/465 C
4,062,885  12/1977  Mekhtiev et al. ................ 260/465 C
4,178,304  12/1979  Litvishtov et al. ............. 260/465 C

*Primary Examiner*—Dolph H. Torrence
*Attorney, Agent, or Firm*—Lilling & Greenspan

[57] ABSTRACT

The present invention relates to methods for preparing aromatic nitriles and, more specifically, to a method for preparing phthalonitriles.

The present method for preparing phthalonitriles resides in subjecting xylene to oxidative ammonolysis at a temperature of 340° to 480° C. in the presence of a catalyst having the following composition (in weight percent):

antimony oxide: 1 to 25
bismuth oxide: 1 to 20
vanadium or molybdenum oxide: 0.2 to 15
ferric oxide: 0.1 to 25
carrier: the balance The method of the present invention will find application in the production of highly heat-resistant polyamide and polyester fibres, new types of xylylenediisocyanate, plastics, phthalocyanine dyes, as well as for producing terephthalic and isophthalic acids and other materials.

3 Claims, No Drawings

METHOD FOR PREPARING PHTHALONITRILES

FIELD OF THE ART

The present invention relates to the production of aromatic dinitriles and, more specifically, to a method for preparing phthalonitriles.

BACKGROUND ART

Known in the art is a method for preparing phthalonitriles by oxidative ammonolysis of xylene in the presence of a catalyst consisting of a mixture of vanadium oxide and molybdenum oxide deposited onto alumina activated by compounds containing cerium, manganese, tin, bismuth, antimony, titanium, lithium, sodium and potassium (in an amount of from 0.1 to 50% by the total weight of vanadium and molybdenum). Upon passing through the catalyst a mixture containing 0.77% by weight of p-xylene, 7.22% by weight of ammonia and 92.05% by weight of air during the contact time of 0.77 sec, at the temperature of 460° C., the maximum yield of terephthalontrile is equal to 95.4% by weight, that of isophthalonitrile is 85% by weight, the yield of orthophthalonitrile is 80% by weight as calculated for the employed xylene. Under these conditions the catalyst capacity relative to terephthalonitrile is 72.4 g/l of the catalyst per hour; the catalyst capacity relative to isophthalonitrile is 60 g/l of the catalyst per hour (cf. U.S. Pat. No. 3,870,743).

Also known in the art is a method for preparing terephthalonitrile by way of oxidative ammonolysis of p-xylene with recycle of the unreacted starting hydrocarbon and intermediate nitriles in the presence of a catalyst consisting of 1.3% by weight of $V_2O_5$ and 8.1% by weight of $Sb_2O_3$ deposited onto alumina. At the temperature of 454° C., space rate of 1,100 hr$^{-1}$ conversion of p-xylene per pass is 50%, selectivity relative to terephthalonitrile is 33 mol.%. The catalyst capacity relative to terephthalonitrile under these conditions is equal to 62 g/l of the catalyst per hour (cf. U.S. Pat. No. 3,497,545).

Another method stipulating the use of the same catalyst (1.3% by weight of $V_2O_5$ and 8.1% by weight of $Sb_2O_3$) and contracting thereof with p-xylene, ammonia and steam (1.5:82.5:6.0:10% by volume) makes it possible to produce terephthalonitrile with the selectivity about 80 mol.% at the 100% conversion of p-xylene (cf. U.S. Pat. No. 3,393,220).

French investigators have studied the reaction of oxidative ammonolysis of p-xylene in the presence of $V_2O_5$, V-Mo, Ti-Mo and Sn-Mo catalysts. The maximum yield of terephthalonitrile of 79% by weight is reached when $V_2O_5$ is used as the catalyst. The process temperature is maintained within the range of from 415° to 460° C., molar ratio of p-xylene:ammonia:air is equal to 1:10:100 (cf. Bull. Soc. Chim. France, 1975, Nos. 11-12, pp. 2617-2621).

Known is a method for preparing terephthalonitrile by way of oxidative ammonolysis of p-xylene or diethylbenzene in a stationary or fluidized bed of a catalyst consisting of oxides of vanadium, chromium, boron, phosphorus (atomic ratio between the elements being equal to 1:(0.5-2):(0.1-1.2):(0.01-0.3)) deposited onto silica gel. Passing a mixture consisting of 1.2% by volume of p-xylene, 9.6% by volume of ammonia and 80.2% by volume of air over this catalyst at the temperature of 305° C. over the contact time of 6 sec results in the content of terephthalonitrile in the reaction products equal to 85.2 mol.%. Capacity of the catalyst relative to terephthalonitrile is equal to 14 g/l of the catalyst per hour.

Known in the art is a method for preparing terephthalonitrile by way of oxidative ammonolysis of p-xylene at the temperature of 360° C. and the contact time of 6 sec in the presence of a catalyst, i.e. vanadium oxide supported on alumina. The yield of terephthalonitrile is 70% by weight (cf. British Pat. No. 796,765).

A principal disadvantage of the above-discussed methods resides in an insufficient yield of the desired product and a low capacity of the catalyst.

Also known in the art is a method for preparing phthalonitriles by way of oxidative ammonolysis of xylene. The process is conducted at a temperature within the range of from 340° to 380° C., the molar ratio between xylene, ammonia and air oxygen of 1:7:20, contact time of from 0.6 to 7 sec in the presence of a catalyst containing 21% by weight of antimony oxide, 3.2% by weight of bismuth oxide, 5% by weight of vanadium oxide or molybdenum oxide supported on alumina. Under these conditions selectivity of terephthalonitrile constitutes 93 mol.%, the catalyst capacity with respect to terephthalonitrile is equal to 67 g/l of the catalyst per hour, in respect of isophthalonitrile and orthophthalonitrile the catalyst capacity is equal to 57 g/l of the catalyst per hour.

This prior art method has a disadvantage residing in a low capacity of the catalyst and an insufficient yield of the desired product.

DISCLOSURE OF THE INVENTION

The present invention is directed to the provision of such a method for preparing phthalonitriles by selecting an appropriate catalyst which would make it possible to increase the yield of the desired product, as well as the output of the product from a unit volume of the catalyst.

This object is accomplished by that in a method for preparing phthalonitriles by way of oxidative ammonolysis of xylene at a temperature within the range of from 340° to 480° C. in the presence of a catalyst containing oxides of antimony, vanadium or molybdenum deposited onto an inert carrier, in accordance with the present invention, use is made of a catalyst additionally containing iron oxide in the following proportions of the components, percent by weight:

antimony oxide: 1 to 25
bismuth oxide: 1 to 20
vanadium oxide or molybdenum oxide: 0.2 to 15
ferric oxide: 0.1 to 25
carrier: the balance.

It is advisable to use the catalyst of the following composition (percent by weight), in order to increase the yield of the desired product:

antimony oxide: 11 to 15
bismuth oxide: 1.0 to 4.0
vanadium oxide or molybdenum oxide: 2.0 to 6.0
ferric oxide: 1.0 to 2.5
carrier: the balance.

It is advisable to use, as the carrier in the abovementioned catalyst, silica gel or alumina.

BEST MODE OF CARRYING OUT THE INVENTION

The method for preparing phthalonitrile is preferably performed in the following manner.

Through a reactor with a stationary or fluidized bed of a catalyst a mixture of xylene, ammonia and oxygen taken in a molar ratio of 1:7–40:4–14 respectively is passed at a temperature within the range of from 340° to 480° C. and contact time of from 0.1 to 6 sec.

The vapour-gas mixture after the reactor is condensed, followed by the recovery of phthalonitriles.

The catalyst is prepared in the following manner. To an acidic solution of bismuth nitrate at a temperature within the range of from 30° to 40° C. under continuous stirring there are added corresponding amounts of soluble salts of antimony, bismuth, iron, vanadium or molybdenum, whereafter the solution temperature is brought to 80°–90° C. and a carrier is added thereto. At this temperature the solution is maintained for 5–6 hours, whereafter it is evaporated.

The resulting mass is dried at a temperature within the range of from 150° to 200° C. for a period of 10 to 12 hours, then calcined at a temperature within the range of from 400° to 600° C. in a current of air or an inert gas for 6 to 8 hours. As a result, a catalyst is obtained consisting of a mixture of oxides of antimony, bismuth, iron, vanadium or molybdenum deposited onto a carrier. The herein-proposed method for preparing phthalonitriles is advantageous over those known in the art in that it ensures a considerable increase in the yield of phthalonitriles together with a higher selectivity of formation thereof.

For a better understanding of the present invention, examples of its specific embodiment are given hereinbelow.

EXAMPLE 1

Into a reactor with the height of 1 m and diameter of 40 mm a catalyst is placed containing 13% by weight of $Sb_2O_3$, 4% by weight of $Bi_2O_3$, 3% by weight of $V_2O_5$, 1.5% by weight of $Fe_2O_3$ deposited onto alumina calcined at the temperature of 900° C. Through the catalyst bed there are passed 8.6 g of p-xylene at the temperature of 400° C., molar ratio of p-xylene to ammonia and oxygen of 1:7, and the contact time of 0.4 sec.

There are obtained 9.9 g of terephthalonitrile. Selectivity is 96 mol.%.

EXAMPLE 2

8.6 g of p-xylene at the temperature of 420° C., molar ratio between p-xylene, ammonia, oxygen equal to 1:40:4 and the contact time of 0.6 sec are passed through a catalyst containing 11% by weight of $Sb_2O_3$, 4% by weight of $Bi_2O_3$, 3% by weight of $V_2O_5$, 1.5% by weight of $Fe_2O_3$ deposited onto alumina calcined at the temperature of 1,000° C.

There are obtained 9.5 g of terephthalonitrile. Selectivity is 92 mol.%.

EXAMPLE 3

8.6 g of p-xylene at the temperature of 420° C., molar ratio between p-xylene, ammonia and oxygen equal to 1:7:9, the contact time of 0.3 sec are passed through a catalyst containing 13% by weight of $Sb_2O_3$, 4% by weight of $Bi_2O_3$, 3% by weight of $V_2O_5$, 2.5% by weight of $Fe_2O_3$ deposited onto alumina calcined at the temperature of 900° C.

There are obtained 10 g of terephthalonitrile. Selectivity is 98 mol.%.

EXAMPLE 4

8.6 g of p-xylene at the temperature of 450° C., molar ratio of p-xylene, ammonia and oxygen equal to 1:7:5.5, the contact time of 0.5 sec are passed through a catalyst containing 15% by weight of $Sb_2O_3$, 2% by weight of $Bi_2O_3$, 2% by weight of $V_2O_5$, 2.5% by weight of $Fe_2O_3$ deposited onto silica gel calcined at the temperature of 600° C.

There are obtained 9.1 g of terephthalonitrile. Selectivity is 88 mol.%.

EXAMPLE 5

8.6 g of p-xylene at the temperature of 420° C., molar ratio between p-xylene, ammonia and oxygen equal to 1:7:7 and the contact time of 0.4 sec are passed through a catalyst containing 13% by weight of $Sb_2O_3$, 4% by weight of $Bi_2O_3$, 3% by weight of $V_2O_5$, 1.0% by weight of $Fe_2O_3$ deposited onto silica gel calcined at the temperature of 800° C.

There are obtained 9.5 g of terephthalonitrile. Selectivity is 92 mol.%.

EXAMPLE 6

8.6 g of p-xylene at the temperature of 420° C., molar ratio between p-xylene, ammonia and oxygen of 1:8:7, the contact time of 0.4 sec are passed through a catalyst containing 13% by weight of $Sb_2O_3$, 1% by weight of $Bi_2O_3$, 3% by weight of $V_2O_5$, 2.5% by weight of $Fe_2O_3$ deposited onto alumina calcined at the temperature of 1,300° C.

There are obtained 9.3 g of terephthalonitrile. Selectivity is 90.5 mol.%.

EXAMPLE 7

8.6 g of p-xylene, at the temperature of 420° C., molar ratio between p-xylene, ammonia and oxygen equal to 1:8:7, the contact time of 0.4 sec are passed through the catalyst containing 11% by weight of $Sb_2O_3$, 3% by weight of $Bi_2O_3$, 6% by weight of $V_2O_5$, 1.5 by weight of $Fe_2O_3$ deposited onto alumina calcined at the temperature of 1,000° C.

There are obtained 9.63 g of terephthalonitrile. Selectivity is 93.5 mol.%.

EXAMPLE 8

8.6 g of p-xylene at the temperature of 420° C., molar ratio between p-xylene, ammonia and oxygen equal to 1:10:4, the contact time of 2 sec are passed through a catalyst containing 1% by weight of $Sb_2O_3$, 20% by weight of $Bi_2O_3$, 15% by weight of $V_2O_5$, 25% by weight of $Fe_2O_3$ deposited onto alumina calcined at the temperature of 1,300° C.

There are obtained 4.75 g of terephthalonitrile. Selectivity is 46 mol.%.

EXAMPLE 9

8.6 g of p-xylene at the temperature of 480° C., molar ratio between p-xylene, ammonia and oxygen of 1:10:14, the contact time of 0.1 sec are passed through a catalyst containing 25% by weight of $Sb_2O_3$, 1% by weight of $Bi_2O_3$, 0.2% by weight of $V_2O_5$, 0.1% by weight of $Fe_2O_3$ deposited onto silica gel calcined at the temperature of 600° C.

There are obtained 3.3 g of terephthalonitrile. Selectivity is 32.8 mol.%.

EXAMPLE 10

8.6 g of m-xylene at the temperature of 400° C., molar ratio between m-xylene, ammonia and oxygen equal to 1:10:8, the contact time of 0.5 sec are passed through a catalyst containing 13% by weight of $Sb_2O_3$, 4% by weight of $Bi_2O_3$, 3% by weight of $V_2O_5$, 0.5% by weight of $Fe_2O_3$ deposited onto alumina calcined at the temperature of 900° C.

There are obtained 9.5 g of isophthalonitrile.
Selectivity is 92 mol.%.

EXAMPLE 11

8.6 g of m-xylene, at the temperature of 340° C., molar ratio between m-xylene, ammonia and oxygen of 1:8:7, the contact time of 4.5 sec are passed through a catalyst containing 15% by weight of $Sb_2O_3$, 7% by weight of $Bi_2O_3$, 20% by weight of $V_2O_5$, 1% by weight of $Fe_2O_3$ deposited onto silica gel calcined at the temperature of 900° C.

There are obtained 4.6 g of isophthalonitrile.
Selectivity is 44% by weight.

EXAMPLE 12

8.6 g of p-xylene at the temperature of 400° C., molar ratio between p-xylene, ammonia and oxygen equal to 1:10:7, the contact time of 1 sec are passed through a catalyst containing 10% by weight of $Sb_2O_3$, 3% by weight of $Bi_2O_3$, 5% by weight of $MoO_3$, 1.4% by weight of $Fe_2O_3$ deposited onto alumina calcined at the temperature of 900° C.

There are obtained 9.95 g of terephthalonitrile.
Selectivity is 97 mol.%.

EXAMPLE 13

8.6 g of p-xylene, at the temperature of 340° C., the molar ratio between p-xylene, ammonia and oxygen equal to 1:10:6, the contact time of 6 sec are passed through a catalyst containing 25% by weight of $Sb_2O_3$, 1% by weight of $Bi_2O_3$, 15% by weight of $MoO_3$, 0.1% by weight of $Fe_2O_3$ deposited onto alumina calcined at the temperature of 1,300° C.

There are obtained 4.9 g of terephthalonitrile.
Selectivity is 47 mol.%.

EXAMPLE 14

8.6 g of p-xylene, at the temperature of 480° C., molar ratio between p-xylene, ammonia and oxygen equal to 1:15:5, the contact time of 0.2 sec are passed through a catalyst containing 1% by weight of $Sb_2O_3$, 20% by weight of $Bi_2O_3$, 2% by weight of $MoO_3$, 25% by weight of $Fe_2O_3$ deposited onto silica gel calcined at the temperature of 1,300° C.

There are obtained 3.2 g of terephthalonitrile.
Selectivity is 31 mol.%.

EXAMPLE 15

8.6 g of m-xylene, at the temperature of 420° C., molar ratio between m-xylene, ammonia and oxygen equal to 1:12:6, the contact time of 0.8 sec are passed through a catalyst containing 10% by weight of $Sb_2O_3$, 2% by weight of $Bi_2O_3$, 6% by weight of $MoO_3$, 0.5% by weight of $Fe_2O_3$ deposited onto alumina calcined at the temperature of 900° C.

There are obtained 9.6 g of isophthalonitrile.
Selectivity is 93 mol.%.

EXAMPLE 16

8.6 g of m-xylene, at the temperature of 480° C., molar ratio between m-xylene, ammonia, oxygen equal to 1:17:8, the contact time of 1.5 sec, are passed through a catalyst containing 1% by weight of $Sb_2O_3$, 20% by weight of $Bi_2O_3$, 2% by weight of $V_2O_5$, 25% by weight of $Fe_2O_3$ deposited onto silica gel calcined at the temperature of 1,000° C.

There are obtained 4 g of isophthalonitrile.
Selectivity is 39 mol.%.

EXAMPLE 17

8.6 g of m-xylene, at the temperature of 340° C., molar ratio between m-xylene, ammonia and oxygen equal to 1:10:6, the contact time of 1 sec, are passed through a catalyst containing 25% by weight of $Sb_2O_3$, 1% by weight of $Bi_2O_3$, 15% by weight of $MoO_3$, 0.1% by weight of $Fe_2O_3$ deposited onto alumina calcined at the temperature of 1,300° C.

There are obtained 3.1 g of isophthalonitrile.
Selectivity is 30.1 mol.%.

EXAMPLE 18

8.6 g of o-xylene, at the temperature of 400° C., molar ratio between o-xylene, ammonia and oxygen equal to 1:25:6, the contact time of 1 sec, are passed through a catalyst containing 10% by weight of $Sb_2O_3$, 2% by weight of $Bi_2O_3$, 4% by weight of $V_2O_5$, 1% by weight of $Fe_2O_3$ deposited onto alumina calcined at the temperature of 900° C.

There are obtained 9.5 g of o-phthalonitrile.
Selectivity is 92 mol.%.

EXAMPLE 19

8.6 g of o-xylene, at the temperature of 420° C., molar ratio between o-xylene, ammonia and oxygen equal to 1:35:6, the contact time of 2 sec, are passed through a catalyst containing 3% by weight of $Sb_2O_3$, 10% by weight of $Bi_2O_3$, 14% by weight of $V_2O_5$, 6% by weight of $Fe_2O_3$ deposited onto silica gel calcined at the temperature of 700° C.

There are obtained 9.7 g of o-phthalonitrile.
Selectivity is 94 mol.%.

EXAMPLE 20

8.6 g of o-xylene, at the temperature of 380° C., molar ratio between o-xylene, ammonia and oxygen equal to 1:15:10, the contact time of 3 sec, are passed through the catalyst containing 15% by weight of $Sb_2O_3$, 7% by weight of $Bi_2O_3$, 20% by weight of $V_2O_5$, 3% by weight of $Fe_2O_3$, deposited onto alumina calcined at the temperature of 900° C.

There are obtained 4.7 g of o-phthalonitrile.
Selectivity is 46 mol.%.

INDUSTRIAL APPLICABILITY

Phthalonitriles are useful in the manufacture of highly heat-resistant polyamide and polyester fibres, new types of xylylenediisocyanate plastics, phthalocyanine dyes, and for the production of terephthalic and isophthalic acids, as well as other materials possessing certain valuable properties.

We claim:

1. A method for preparing phthalonitriles by oxidative ammonolysis of xylene at a temperature within the range of from 340° to 480° C. in the presence of a catalyst containing oxides of antimony, bismuth, vanadium, or molybdenum deposited onto an inert carrier, characterized in that a catalyst is used additionally containing ferric oxide, the components being present in the following proportions, percent by weight:
antimony oxide: 1-25
bismuth oxide: 1-20
vanadium oxide or molybdenum oxide: 0.2-15
ferric oxide: 0.1-25
carrier: the balance.

2. A method according to claim 1, characterized in that a catalyst is used having the following composition, percent by weight:
antimony oxide: 11-15
bismuth oxide: 1.0-4.0
vanadium oxide or molybdenum oxide: 2.0-6.0
ferric oxide: 1.0-2.5
carrier: the balance.

3. A method according to claim 1 or 2, characterized in that a catalyst is used which contains silica gel or alumina as the carrier.

* * * * *